United States Patent [19]
Rose et al.

[11] Patent Number: 4,896,673
[45] Date of Patent: Jan. 30, 1990

[54] METHOD AND APPARATUS FOR STONE LOCALIZATION USING ULTRASOUND IMAGING

[75] Inventors: Freeman H. Rose, Del Mar; Charles D. McGregor, Laguna Beach; Prabodh Mathur, El Toro, all of Calif.

[73] Assignee: Medstone International, Inc., Costa Mesa, Calif.

[21] Appl. No.: 219,208

[22] Filed: Jul. 15, 1988

[51] Int. Cl.$^4$ .............................................. A61B 8/00
[52] U.S. Cl. ............................ 128/660.03; 128/24 A
[58] Field of Search ................ 128/24 A, 328, 660.03, 128/782

[56] References Cited
U.S. PATENT DOCUMENTS

| | | | |
|---|---|---|---|
| 3,051,167 | 8/1962 | Fry et al. ............................ | 128/24 A |
| 4,787,371 | 11/1988 | Grasser et al. .................... | 128/24 A |
| 4,813,436 | 3/1989 | Au ....................................... | 128/782 |
| 4,821,729 | 4/1989 | Makofski et al. ............... | 128/660.03 |

Primary Examiner—Ruth S. Smith
Assistant Examiner—Krista Pfaffle
Attorney, Agent, or Firm—Lyon & Lyon

[57] ABSTRACT

The present disclosure relates to a method and apparatus for localizing an object in space, such as a gallstone in a human, using stereo imaging and ultrasound imaging. The localization system is described in connection with a dry table shock wave lithotripter, and uses a conventional ultrasound imaging system but wherein the ultrasound transducer has been modified to enable its location in space to be readily determined automatically. This is accomplished by providing a hood fixed to this transducer, the hood having a plurality of reference points which may be in the form of light sources such as LEDs. This hood is imaged by head and foot video cameras. By calibrating the cameras with respect to a reference point, calibrating the focal point of the shock wave system with respect to the reference point, and knowing the relationship of the hood to the ultrasound transducer, the position of the stone with respect to the reference point can be determined by ultrasound imaging of the stone, along with suitable storage of the ultrasound and camera images, digitizing and processing of these images. Given this information, the patient with the stone can be suitably moved so as to position the stone at the focal point of the shock wave generating system.

14 Claims, 5 Drawing Sheets

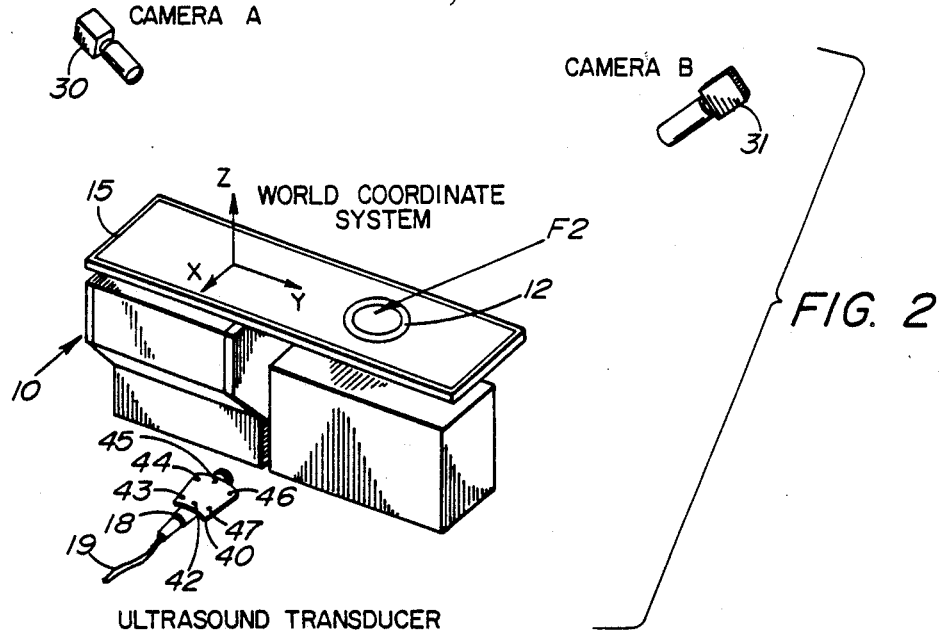
FIG. 2
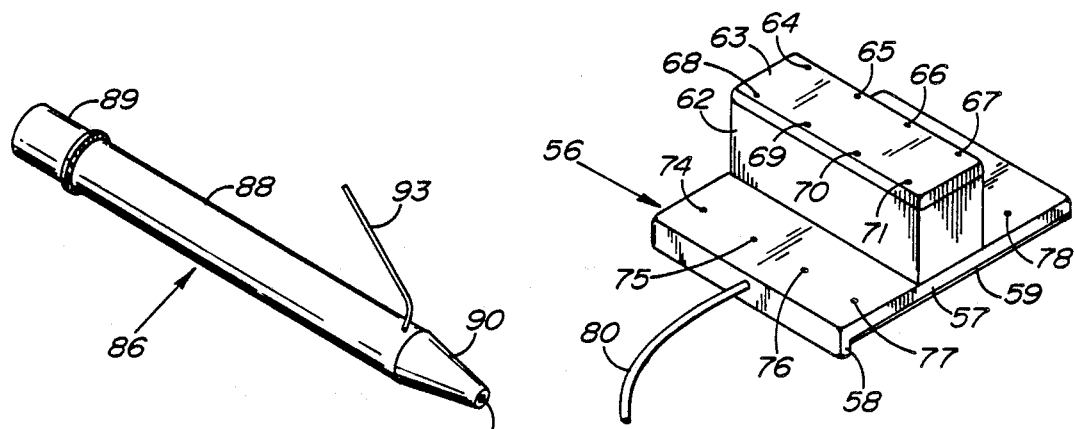
FIG. 4
FIG. 3
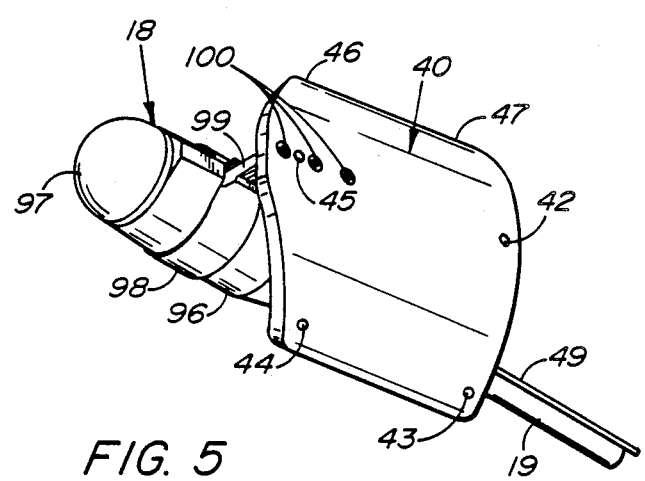
FIG. 5

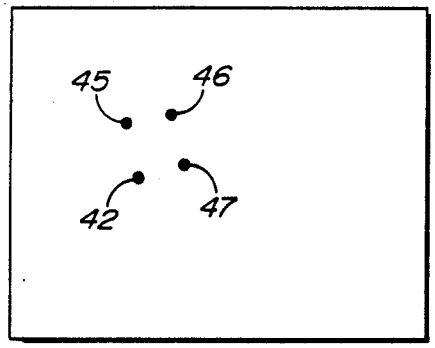
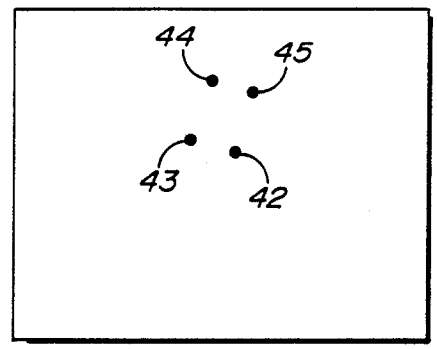
FIG. 6a          FIG. 6b
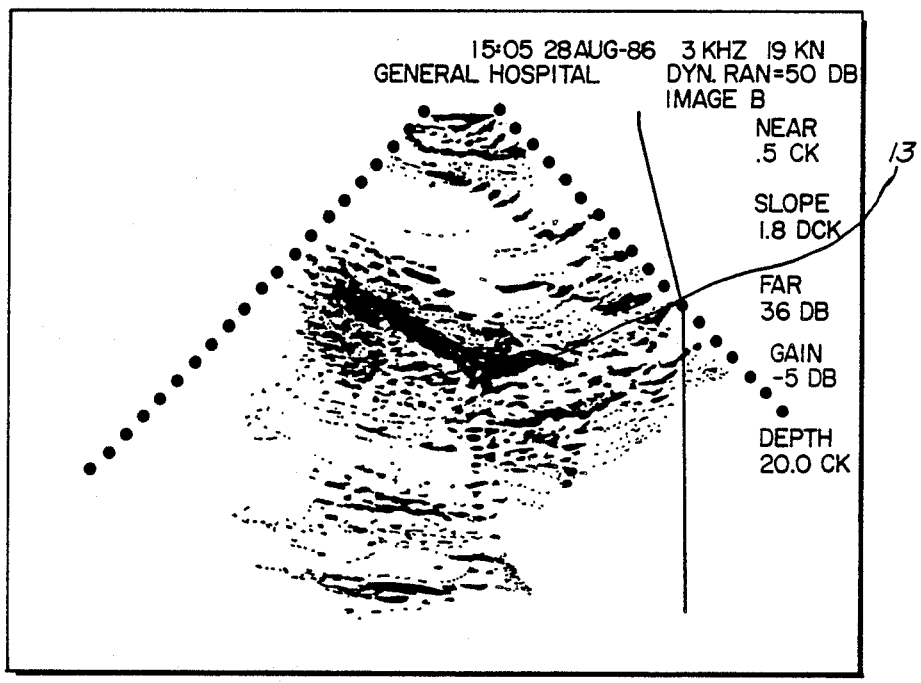
FIG. 7

METHOD AND APPARATUS FOR STONE LOCALIZATION USING ULTRASOUND IMAGING

SUMMARY OF THE INVENTION

The present invention relates to localization of objects in space, and more particularly to the localization of gallstones and the like using ultrasound imaging.

BACKGROUND OF THE INVENTION

Systems and methods have been developed for fragmentation of kidney stones and gallstones by utilizing shock waves generated by a suitable source and reflector system. Several systems and methods of this type have been devised. The technique is generally referred to as shock wave lithotripsy. The early approaches have involved immersing the patient in water and directing the shock wave, generated by an underwater spark discharge, at the stone. In such method and device, high pressure shock waves are generated by the underwater spark discharge and are focused by an ellipsoidal reflector toward the stone in the patient. When the shock waves hit the stone, pressure and tensile forces are produced that lead to its fragmentation. Such liberation of energy occurs when there is a change of acoustic impedance from water or body tissue to the stone. That is, pressure and tensile forces are created both when the shock wave enters the stone and when it leaves, and the stone starts to disintegrate into a fine grit or powder. A more recent development is the dry table system, such as the Medstone International, Inc. Model 1050ST Lithotripter System, which does not require the patient to be immersed in water for the shock wave treatment.

These shock wave systems also require the stones to be appropriately located and positioned with respect to the shock wave, and the localization systems commonly used involve X-ray imaging. Basically, the physician takes several X-rays to determine where the stone is in the body, such as a stone in the right kidney. Prior to the application of the shock waves, two oblique X-rays (head and foot) are taken and the resultant developed films are digitized. Then, through automatic computations by triangulation the location of the stone is determined with reference to the focal point of the shock wave equipment.

A description of X-ray location systems in kidney lithotripters can be found, for example, in U.S. Pat. Nos. 4,669,483 and 4,705,026.

While X-ray localization is used in the case of kidney stones, ultrasound imaging can be used in the case of gallstones and it is actually easier to find and locate gallstones through the use of ultrasound rather than X-rays. In addition, the ultrasound techniques are safer inasmuch as there does not need to be any exposure to X-rays. However, X-ray localization of such stones has continued to be used because no suitable non X-ray accurate localization technique has been developed.

SUMMARY OF THE INVENTION

The present invention is directed to a method and apparatus for enabling an object to be located with respect to a reference point using ultrasound imaging or the like. In the shock wave treatment of gallstones in a human, for example, it is necessary to precisely locate and position the gallstone with respect to the focal point (F2) of the shock wave equipment. According to an exemplary embodiment of the present invention, and wherein a dry table shock wave lithotripter is used, a pair of video cameras detect the position of an ultrasound transducer which is used for imaging the stone in the patient. The location of the stone in the ultrasound image defines the relationship of the stone to the ultrasound transducer. The location and orientation of the transducer itself are arbitrary and only depend upon the way the transducer is held by the operator.

The two cameras, along with suitable computer hardware and software for performing image analysis and computations, are utilized to determine the relationship of the ultrasound transducer with respect to a fixed, known coordinate system called the World Coordinate System (WCS). The WCS is defined during initial calibration which involves calibrating the cameras with a calibration fixture related to the WCS, and calibrating the focal point (F2) of the shock wave system with respect to the WCS. In addition, and according to an exemplary embodiment of the present invention, a location device referred to as a "hood" is attached to the ultrasound transducer, and the location of the ultrasound transducer with respect to the hood is calibrated. The hood provides a plurality of reference points, such as from sources on the hood, which are viewed and imaged by the cameras. The present system essentially utilizes triangulation and image processing of stereoscope camera images to find the location of the stone.

With the patient positioned on the positioning table of the shock wave lithotripter, as well as the system components calibrated as described, the hood of the ultrasound transducer imaged by the cameras, and the operator determining that a satisfactory ultrasound image exists, sufficient information is available to readily calculate the distance of the stone from the focal point (F2) of the shock wave system. The operator then can be prompted to move the patient by this distance to thereby position the stone at F2. The shockwave treatment can then begin. During the shock wave administration, the stone disintegration can be monitored in real time using ultrasound imaging if desired. This provides a verification of the localization independent of computer calculations, lithotripter table movement and operator responses to image digitization prompts.

The techniques and apparatus of the present invention do not require the prior X-ray imaging techniques which involve two oblique X-rays for positioning of stones at F2. In such prior systems, these X-rays image the stone and projection of an F2 target. In such prior systems, the associated computer calculates the distance of the stone from F2, and since the location of the F2 target is set during calibration, this information is sufficient to determine the patient movement then required to locate the stone at F2. Confirmation X-rays are required after patient movement which verify the accuracy of the localization. These confirmation X-rays provide a verification independent of computer calculations, lithotripter table movement and operator responses to film digitization prompts. However, it is necessary to use the bulky and cumbersome X-ray equipment.

Accordingly, it is a principal object of the present invention to provide an improved form of localization system for an object.

It is another object of this invention to provide a new form of stone localization using ultrasound imaging.

Another object of this invention is a method and system for finding the location of a stone in a patient through triangulation and image processing of stereoscopic images and an ultrasound image.

BRIEF DESCRIPTION OF DRAWINGS

These and other objects and features of the present invention will become better understood through a consideration of the following description taken in conjunction with the drawings in which:

FIG. 2 is a perspective view further illustrating components of the localization system;

FIG. 3 is a perspective view of a camera calibration fixture of the present invention;

FIG. 4 is shock wave focal point location calibration fixture of the present invention;

FIG. 5 is a perspective view of an ultrasound transducer and hood according to the present invention;

FIGS. 6a and 6b illustrate typical images from head and foot cameras of the present invention;

FIG. 7 is a typical ultrasound image;

DETAILED DESCRIPTION

An exemplary embodiment of the present invention will now be described, first with reference to FIGS. 1 and 2. While the concepts of the present invention will be described with reference to location of the stone by ultrasound images in a dry table shock wave lithotripter system for gallstone treatment, the concepts are applicable to localization of kidney stones and other objects.

Figure 1:
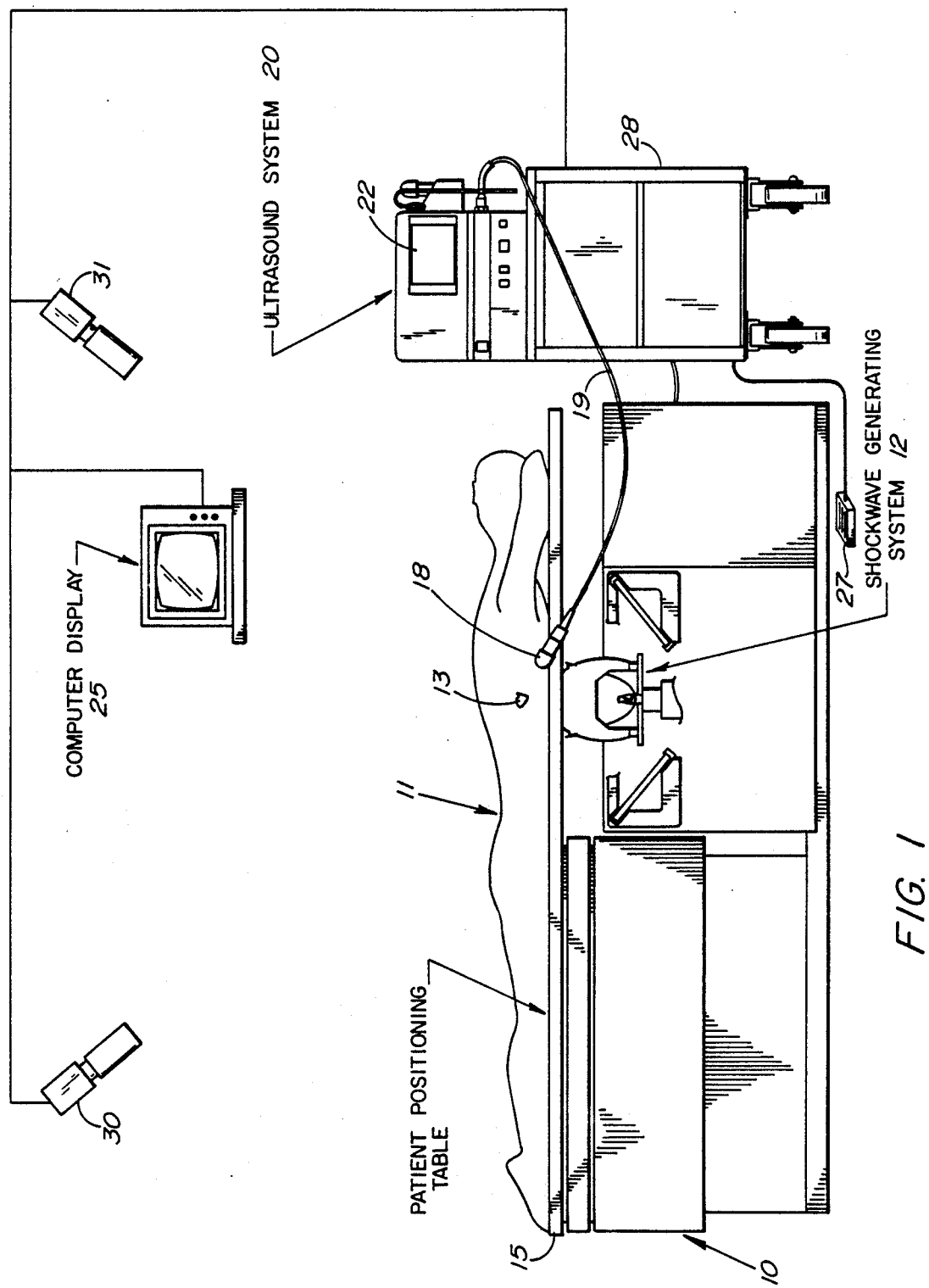
FIG. 1 is a general elevational view of a localization system according to the present invention.

Turning first to FIG. 1, a conventional dry table shock wave lithotripter 10, such as the Model 1050ST lithotripter system manufactured by Medstone International, Inc. of Costa Mesa, Calif., is shown with a patient 11 positioned thereon. The shock wave generating system is illustrated generally at 12 for treating a gallstone 13. The lithotripter 10 has a table 15 which is movable in the X, Y and Z directions (note the direction of the WCS coordinates in FIG. 2) so as to enable the stone 13 and the patient 11 to be positioned with respect to the focal point F2 of the shock wave generating system 12 (the stone 13 is shown at F2 in FIG. 1).

An ultrasound transducer 18 is used to locate the stone 13, and the transducer is connected by a cable 19 to an ultrasound imaging system 20. The ultrasound system 20 and transducer or probe 18 are conventional and provide an image on a monitor 22 of the ultrasound system 20. A typical image is shown in FIG. 7 as is well known to those skilled in the art. A conventional cursor (not shown) allows the stone to be located in the image by the operator touching the cursor to the appropriate location on the screen 22 in the usual manner. The image also may be shown if desired on a computer display monitor 25 positioned over the lithotripter 10 for convenient viewing by the operator. The monitor can also provide various prompts to the operator.

The system of FIG. 1 further has an overhead imaging system comprising left and right video cameras 30 and 31 which are aimed generally where the patient is to be and in the vicinity of F2 and where the stone is to be positioned. The purpose of these cameras is to detect the location and position of the ultrasound transducer 18. A foot pedal 27 is provided to enable the operator to capture images when desired from the cameras 30 and 31 and from the ultrasound transducer system. A computer system 28 can be housed in the ultrasound system cabinet. The ultrasound system 20, cameras 30 and 31, display 25, lithotripter table positioning system, shock wave generating system 12, and foot pedal 27 are all connected to the computer as diagrammatically indicated in FIG. 1.

Turning now particularly to FIGS. 2 and 5, and according to the concepts of the present invention, the ultrasound transducer 18 preferably includes locating means in the form of a hood 40 affixed thereto and which is imaged by the cameras 30 and 31. The hood 40 includes means by which it can be readily imaged by the cameras 30 and 31, and in the exemplary embodiment shown in FIGS. 2 and 5 includes six sources, which may be LED's or infrared lamps or associated retro-reflectors (corner cube prisms) 42 through 47. These sources may be suitably energized through a cable 49 attached to the ultrasound transducer cable 19. These sources 42 through 47 on the hood 40 allow the cameras 30 and 31 to image the hood as the operator moves the ultrasound transducer 40 in localizing the stone. The sources thus provide reference points which can be detected to enable the location of the hood to be accurately determined. Once the operator is satisfied with the ultrasound image obtained, that image is captured or stored and, at the same time, the images of the hood are stored. This information allows suitable computations to be made by the associated computer system 28 to define the relationship of the stone to the ultrasound transducer. Further details of attachment of the hood 40 to the ultrasound transducer 18 and calibration thereof will be described later with reference to FIGS. 5, 8 and 9.

Before discussing further details of construction and operation of the present method and apparatus, it may be helpful to briefly discuss the sequence of operations involved in locating the stone 13 with respect to the focal point F2 of the shock wave generating system. The cameras 30 and 31 are calibrated (note 32 in FIG. 8) using a camera calibration fixture or jig as shown in FIG. 3 and which will be discussed in greater detail later. This fixture is imaged by each respective camera 30 and 31 individually. Known points on the jig are defined in a suitable reference system called herein a World Coordinate System (WCS). Using the images of the fixture, the associated computer 28 determines the parameters of each camera which defines its location, orientation, origin and focal length. The WCS is implicitly defined during this camera calibration. The relationship of the hood to the ultrasound probe is already known (29 in FIG. 8) in the construction of the same which will be described later.

Figure 8:
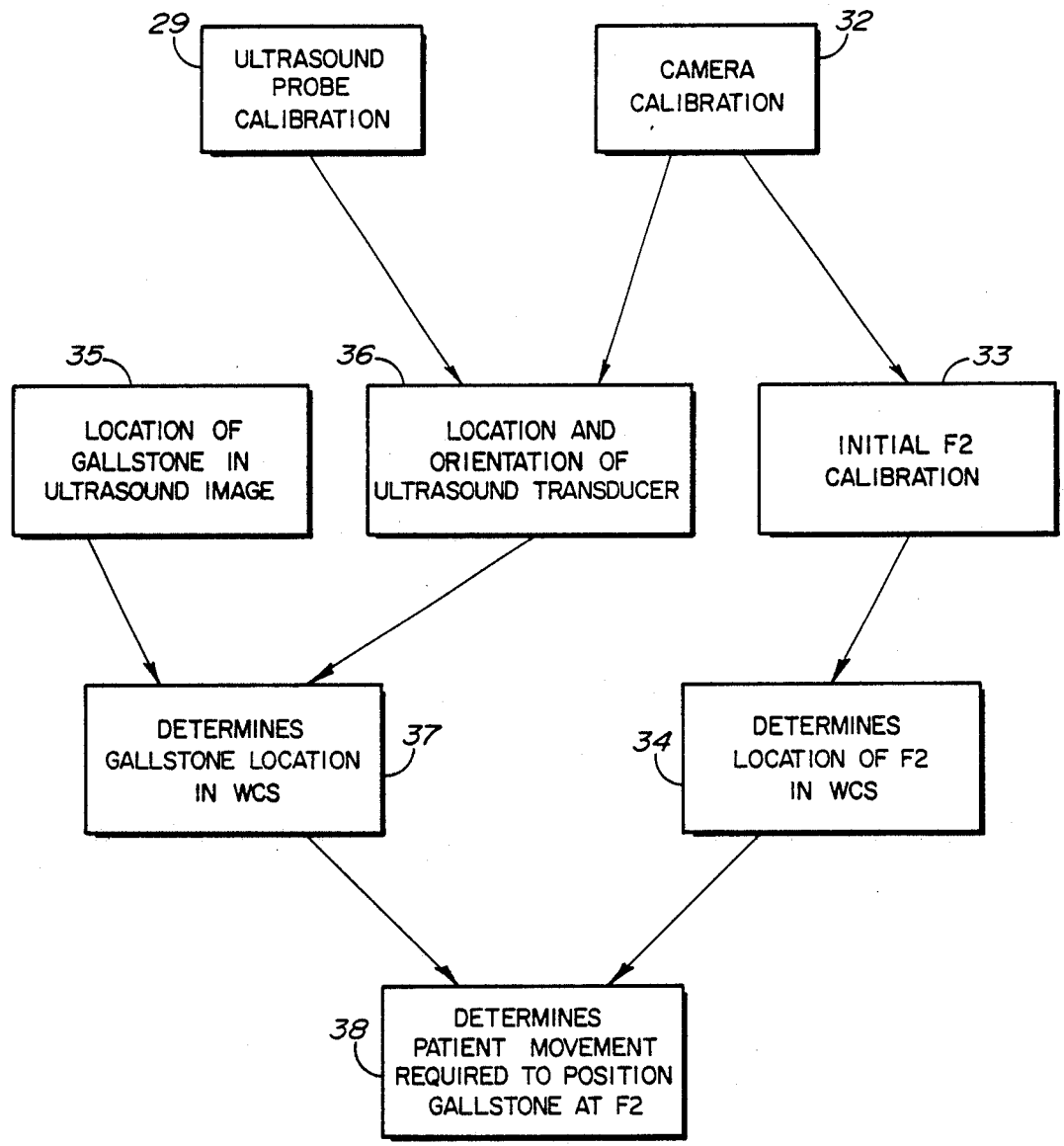
FIG. 8 is a flow chart illustrating calibration and location steps in the localization of the gallstone.

Additionally, the location of F2 is calibrated as indicated at 33 in FIG. 8. This is accomplished by using an F2 location calibration fixture as shown in FIG. 4 and which will be described in more detail later. This fixture is inserted into the ellipse shaped reflector of the shock wave generating system 12 of FIG. 1 such that the tip of the fixture can be imaged by the two cameras 30 and 31. The computer then determines the location of F2 in the WCS as indicated at 34. As will be apparent, these camera and F2 calibrations will hold as long as the physical relationship between the camera 30 and 31 and lithotripter table 15 does not change. F2 calibration has to be performed every time the cameras are calibrated since camera calibration also defines the WCS.

Next, the stone 13 is imaged using the ultrasound transducer 18 in a conventional manner as indicated at 35. The external points on the hood fixed to the ultrasound transducer are imaged by the cameras 30 and 31 as indicated at 36 to detect the location and orientation of the ultrasound transducer. When the operator determines that the ultrasound image of the stone is acceptable according to conventional practice by viewing the same on the CRT 22, the foot switch 27 is depressed and the images from the cameras 30 and 31 and the ultrasound are captured by the computer 28 simultaneously. The operator then marks the location of the stone in the ultrasound image on the CRT 22 using a cursor (not shown) in a conventional manner. The computer scales the distance of the stone from the transducer tip in screen coordinates to the physical distance using a pre-programmed scaling factor, and this determines the location of the stone in relation to the ultrasound transducer based on probe calibration 29 since the initial calibration includes calibration of the ultrasound transducer with respect to the points on the hood fixed to the ultrasound transducer.

The two images from the overhead cameras are processed. The images of the external points of the hood fixed to the ultrasound transducer as viewed by the two cameras determine the position of the hood in the WCS. Using conventional coordinate transformation techniques, the mathematical relationship between the coordinate system defining the transducer and WCS is established. This transformation is then applied to the location of the stone determined previously in relation to the hood. The location of the stone in relation to WCS is therefore determined as indicated at 37.

As will be apparent to those skilled in the art, at this point the associated computer 28 thus contains the following information:

1. Location of F2 in WCS, from initial calibration; and
2. Location of the stone in WCS. A simple subtraction operation determines the distance the lithotripter table 15 must be moved to position the stone 13 at F2.

Stated briefly, the location of the stone with reference to F2 is determined by effectively imaging the location of the ultrasound transducer (via the points on the hood 40) with the cameras 30 and 31, and storing the camera images and the ultrasound image when a suitable ultrasound image exists as determined by the operator. The location of the transducer with respect to the hood is known from its construction, the location of each of the two camera 30 and 31 with respect to WCS is known, and the location of F2 with respect to WCS is known. The image of the stone provided by the ultrasound transducer system 20 tells the position of the stone with respect to the transducer, and the camera images of the hood affixed to the ultrasound transducer tell the location of the ultrasound transducer with respect to the WCS. The computer then calculates the location of the stone in the WCS to thereby provide information to the operator, as through the computer display 25 in FIG. 1, for adjusting the lithotripter table to thereby position the stone 13 at F2.

During shock wave administration, the stone disintegration can be monitored in real time using ultrasound imaging in a conventional manner. This provides a verification of the localization independent of computer calculations, lithotripter table movement and operator responses to image digitization prompts.

Turning now to a more detailed discussion of the calibration fixtures, camera and ultrasound images, and a flow chart of the present method and apparatus, the camera calibration fixture is illustrated in FIG. 3. This fixture 56 includes a base 57 with a lip 58. A resilient pad 59 may be provided on the underside of the base 57. The base 57 is placed on the top of the lithotripter table 15 (FIGS. 1 and 2) near the shock wave operating system, and the lip 58 can extend downwardly along the side edge of the table 15 to facilitate placement and orientation of the fixture on the table. The fixture includes a raised portion 62 with a cap 63. The cap 63 includes a plurality of sources, such as red LEDs or infrared sources 64 through 71. Two rows of four each of additional sources, only sources 74 through 78 being seen in FIG. 3, are provided on the top of the base 57. Thus, a total of sixteen sources are provided with two rows of four on opposite sides of the top of the base 57 and two rows of four disposed on the cap 63. These sources may include suitable retro-reflectors if desired. The sources are connected through a cable 80 to the associated computer system 28 so as to energize these sources during camera calibration.

The camera calibration fixture is placed on the top of the lithotripter table 15 near the shock wave generating system 12 as noted earlier. The sixteen sources provide known points which are imaged by first one of the cameras 30 or 31 and then by the other. As noted earlier, these points are defined in the World Coordinate System, and the computer determines the parameters of each camera using the images of these sources picked up by the cameras, to thereby define the location, orientation, origin and focal length of each camera and for defining the WCS as noted earlier. Thus, in summary, the fixture 56 is placed on the lithotripter table 15 and one camera 30 or 31 is operated at a time to pick up the images of the sixteen sources. The sources provide bright points serving as known reference points, and the images thereof are analyzed and processed in a conventional manner to provide the camera calibration.

Turning now to the focal point F2 location calibration, an exemplary fixture 86 is shown in FIG. 4. This fixture is essentially in the form of an elongated rod 88 with a base 89 and an upper tip 90. The tip includes a source 91, such as a LED or infrared source and which may include a retro-reflector, like those used in the camera calibration fixture 56 and hood 40. The LED is connected through a cable 93 to the computer system 28 which turns on the source 91 during F2 calibration. The base 89 is configured to fit within the ellipse shaped reflector of the conventional shock wave generating system 12 so that the source 91 extends upwardly from the system 12 and above the lithotripter table 15 so that the source 91 is at F2. The length of the fixture is such that source 91 is at F2. This provides a source 91 which can be imaged by the cameras 30 and 31 to provide the location of F2 to the associated computer system.

Turning again to the hood 40 and particularly to the perspective view thereof in FIG. 5, the ultrasound transducer 18 is conventional and includes an elongated body 96 terminating in the ultrasound probe end 97. The hood 40 is attached to the body 96 of the transducer 18 by a C-shaped clamp 98 having a spacer 99 extending therefrom to which the hood 40 is secured as by screw fasteners 100. It is necessary for the hood 40 to be rigidly affixed to the ultrasound transducer 18 so that the position of the transducer as detected via the sources 42–47 of the hood, can be located and known by the associated computer system 28. The spacer 99 is provided so that the operator can still grasp the body 96 of the transducer 18 by hand underneath, the hood 40 so as not to cover or interfere with the camera views of the sources 42-47.

The hood 40 may have any suitable shape, it only being necessary that the sources 42-47 be visible to the cameras 30 and 31 during movement of the ultrasound transducer 18 in imaging the stone 13. It is preferred that the hood have a slightly curved or arcuate configuration as seen in FIGS. 2 and 5 and to have the trapezoidal outline as shown. It is desirable that the hood be as lightweight and as unobtrusive as possible, consistent with the objective of providing a plurality of reference points thereon to be imaged by the cameras 30 and 31.

FIGS. 6a and 6b illustrate typical head camera (31) and foot camera (30) images of the sources on the hood 40 of FIG. 5. While all six sources or any suitable number, can be imaged by each camera, it has been found preferable with the method and system of the present exemplary embodiment to turn off the two distant sources (which can be done automatically by the computer system 28) during ultrasound imaging. Thus, in the head camera image of FIG. 6a from the head camera 31 (FIG. 2), the two distant sources 43 and 44 on the hood 40 are turned off, and only the sources 42, 45, 46 and 47 are imaged as indicated in FIG. 6a. Similarly, in the foot camera image of FIG. 6b from foot camera 30, the two distant sources 46-47 are turned off and only the sources 42-45 are imaged as shown in FIG. 6b.

FIG. 7 shows a typical conventional ultrasound image provided on the CRT 22 of the ultrasound system 20 of FIG. 1. The stone 13 is generally indicated by the reference numeral 13. The ultrasound imaging involved in the present method and apparatus wherein the stone 13 is imaged with the ultrasound transducer 18 and processed in the ultrasound system 20, and the operator's capturing of the image through use of a cursor are all conventional techniques. However, in conventional practice the ultrasound transducer itself is not located or, in some systems, it may be disposed on a robotic arm to provide feedback signals to give an indication of its location. The present method and apparatus differs significantly in that locator means (e.g., hood 40) are affixed to the ultrasound transducer to allow imaging by an associated camera system to thereby precisely locate the ultrasound transducer without the various errors encountered in a robotic feedback locator system.

Figure 9:
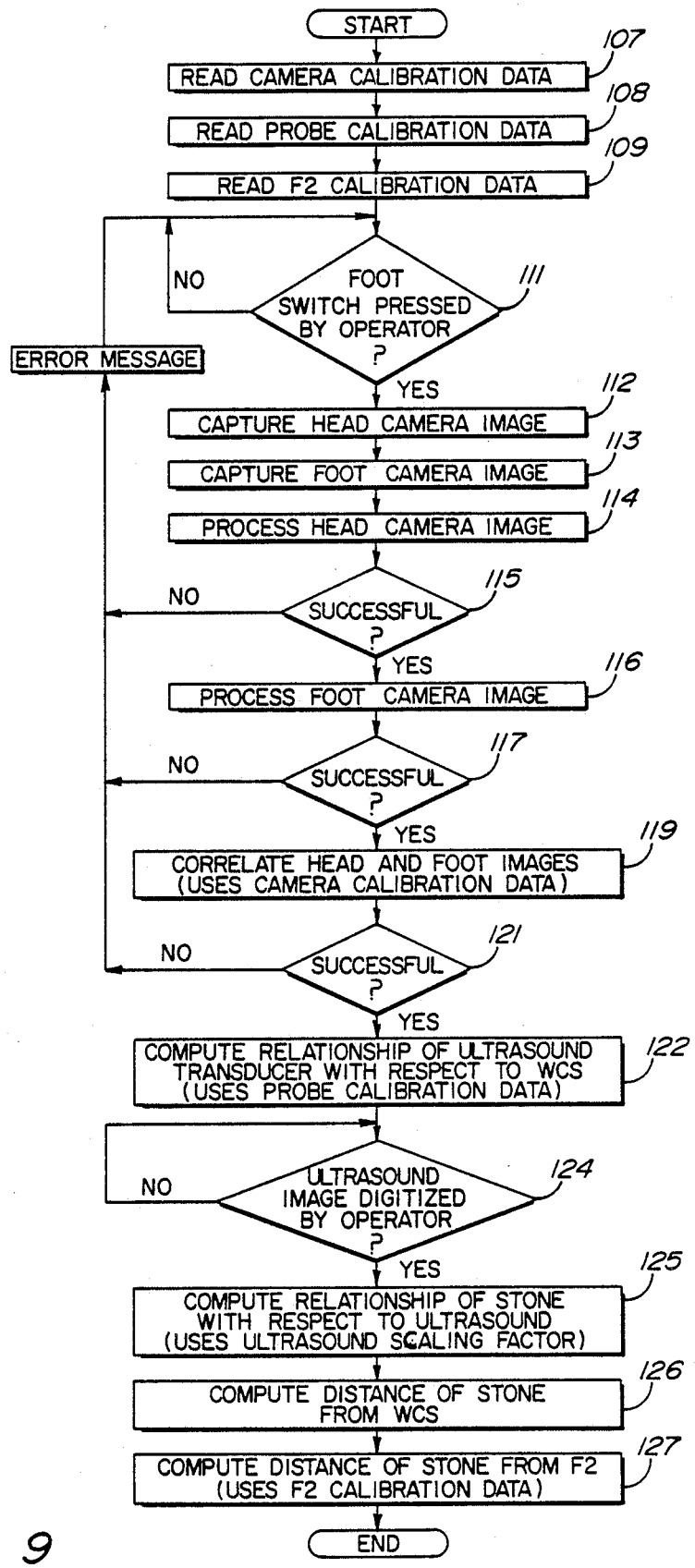
FIG. 9 is an exemplary algorithm for gallstone localizations using camera images and ultrasound.

FIG. 9 illustrates an exemplary algorithm for gallstone localization using camera images and ultrasound. The sequence shown is commenced after calibrating the cameras 30 and 31, calibrating the ultrasound transducer or probe 18 using the hood 40, and calibrating the shock wave generating system focal point F2 using fixture 86 as noted earlier. The respective calibration data is read as indicated at 107-109 in FIG. 9. These operations store the calibration data for the cameras, ultrasound transducer/hood, and focal point F2 so as to enable the subsequent calculation of the location of the stone 13 with respect to WCS (and F2).

The stone is imaged using the ultrasound transducer 18 according to conventional practice. When the operator has determined that the ultrasound image of the stone is acceptable, the foot switch 34 is depressed to capture the images from the cameras 30 and 31 and the ultrasound image simultaneously and store the same in the computer. Suitable prompts can be provided on the computer display 25 to guide the operator through the various steps as will be apparent to those skilled in the art. Thus, when the foot switch 34 is depressed as checked in step 111 in FIG. 9, the head camera 31 and foot camera 30 images can be captured as indicated at 112-113, and the images processed as indicated at 114 and 116 the processing of these images is successful as interrogated at 115 and 117, the images are correlated for correspondence as indicated at 119. The processing steps 114, 116 merely involve digitizing the respective camera images through high pass filtering and thresholding to find the clump of spots in the image (from the sources 42-47) so as to detect the centroid of that clump to provide image resolution. The correlation of step 119 involves standard image processing, such as of the type described in "Depth Perception for Robots" by A. C. Kak, School of Electrical Engineering, Purdue University, West LaFayette, Ind., 47907, Technical Report TR-EE-83-44 October 1983. See also "A System for Extracting Three-Dimensional Images From a Stereo Pair of TV Cameras" by Y. Yakimovsky and R. Cunningham, Computer Graphics and Image Processing 7, 1978, pages 195-120. Once the correlation is complete, the process proceeds from step 121 to step 122 wherein the relationship of the ultrasound transducer 18 is computed with respect to WCS using the probe calibration data discussed subsequently. Thus, the locations of the six sources on the hood 40 are known and therefore the hood and probe relationship to WCS can be readily determined by applying the techniques described in "Robot Manipulators: Mathematics, Programming, and Control" by R. P. Paul, MIT Press Series in Artificial Intelligence, 1981.

After the relationship of the ultrasound transducer 18 is computed with respect to WCS, the computer checks as indicated at 124 if the ultrasound image has been digitized by the operator. This occurs by the operator marking the location of the stone in the ultrasound image using a cursor of the ultrasound system 20 in conjunction with CRT display 22 in a conventional manner. The computer then scales the distance of the stone from the transducer tip in screen coordinates to the physical distance using a suitable ultrasound scaling factor to give the location in millimeters as versus screen pixels by computing the relationship of the stone with respect to the hood, and given the calibration of the hood with respect to the ultrasound transducer, the relationship to WCS is computed as indicated at 125, 126. As explained earlier, the hood 40 relationship to WCS is determined at step 122, and the relationship of the stone with respect to the hood is determined at step 125, and then the distance of the stone 13 from WCS is determined at 126 given that the relationship between the hood 40 and ultrasound transducer 18 is known from earlier calibration step 108. Finally, the computer can then calculate the distance of the stone 13 from the focal point F2 inasmuch as the relationship of F2 to WCS has been determined in the earlier calibration step 109. The computer can provide a suitable display on the computer display 25 (FIG. 1) to indicate to the operator the directions and distances the table 15 should be moved so as to position the patient 11 and therefore the stone 13 at F2 or the table can be moved automatically. Then, shock wave administration can begin.

Accordingly, a new method and apparatus for localizing an object in space, such as a gallstone in a human, through the use of stereo video images and ultrasound imaging is provided.

While embodiments of the present invention have been shown and described, various modifications may be made without departing from the scope of the present invention, and all such modifications and equivalents are intended to be covered.

What is claimed is:

1. A method for gallstone localization using ultrasound imaging for enabling a gallstone to be positioned with respect to a focal point of a shock wave system comprising the steps of
providing an ultrasound image of a gallstone in a patient using an ultrasound transducer by moving the ultrasound transducer adjacent the patient,
detecting the position of the ultrasound transducer by imaging the transducer means by first and second cameras, said cameras means being calibrated with respect to a reference,
storing images of the transducer picked up by the cameras means and processing said images,
capturing said ultrasound image of the gallstone, and
calculating the relationship of the gallstone with respect to the ultrasound transducer using aid ultrasound image of said gallstone and calculating the distance of the stone from the reference using said calculated relationship of the gallstone with respect to the transducer and the detected position of the transducer.

2. A method as in claim 1 wherein
said ultrasound transducer having a hood affixed thereto and wherein the position of the hood with respect to the ultrasound transducer is calibrated, said hood having a plurality of reference points thereon which can are detected by said cameras for determining the position of the hood with respect to the reference.

3. A method as in claim 2 wherein said reference points on said hood comprise a plurality of sources which are viewed and imaged by the cameras.

4. A method as in claim 1 wherein
said first and second cameras comprise a pair of video cameras which are calibrated by positioning a calibration fixture on a dry table lithotripter, said fixture including a plurality of reference points which are imaged first by one video camera and then by the other video camera to calibrate said cameras with respect to the position of the reference, the reference being defined by a World Coordinate System (WCS), and
calibrating the focal point of the shock wave system with respect to the WCS.

5. A method for locating an object in a human patient using ultrasound imaging to enable the object to be positioned with respect to a focal point of a shock wave generating system and wherein the focal point of the shock wave system is calibrated with respect to reference coordinates, comprising the steps of
scanning the patient with an ultrasound transducer means to provide on an ultrasound system monitor an ultrasound image of the stone in the patient
imaging the position of the ultrasound transducer by stereo video cameras means and wherein the camera images the ultrasound transducer means from two different angles and wherein the camera have been calibrated with respect to the reference coordinates,
capturing the ultrasound image and marking the location of the stone in the ultrasound image, and capturing images of the transducer picked up by the cameras,
processing the images from the cameras to
the location of the ultrasound transducer upon capture of the ultrasound image of the object, and
calculating the relationship of the stone with respect to the transducer, calculating the relationship of the stone to the reference coordinates, and calculating the distance of the stone from the focal point.

6. A method as in claim 5 wherein
said ultrasound transducer having affixed thereto and spaced therefrom a hood and wherein the position of the hood is calibrated with respect to the ultrasound transducer, said hood having a plurality of reference points thereon which can be detected by said cameras for determining the position of the hood with respect to the reference coordinates.

7. A method as in claim 6 wherein
said cameras comprises a pair of video cameras displaced from one another and aimed in the general vicinity of the focal point, and
said reference points on said hood comprise a plurality of light sources.

8. A method as in claim 7 wherein
said shock wave system comprises a dry table shock wave lithotripter having a movable table upon which the patient can lay and be moved with respect to the focal point, and including the step of moving said table to position the stone at the focal point.

9. A method as in claim 8 wherein
said cameras are calibrated by positioning a calibration fixture on the table of the lithotripter, said fixture including a plurality of reference points which may be imaged first by one video camera and then by the other video camera to calibrate said cameras with respect to the reference coordinates, the position of the reference coordinates being defined by a World Coordinate System (WCS), and
wherein, the focal point is calibrated by imaging with said cameras a focal point target positioned at the focal point.

10. A method for locating an object within a body using ultrasound imaging to detect the position of the object in the body, comprising the steps of
scanning the body with an ultrasound transducer to provide an ultrasound image of the object,
imaging the position of the ultrasound transducer by stereo video cameras and wherein the cameras image the ultrasound transducer means from two different angles, the cameras being calibrated with respect to reference coordinates,
capturing the ultrasound image and marking the location of the object in the image, and capturing images of the transducer picked up by the cameras,
processing the images from the cameras to determine the location of the ultrasound transducer upon capture of the ultrasound image of the object, and
calculating the relationship of the object with respect to the transducer using said ultrasound image of said object and calculating the relationship of the object to the reference coordinates, using said calculated relationship of the object the respect to the transducer and the detected position of the transducer.

11. A method as in claim 10 wherein said camera means comprise a pair of video cameras displaced from one another and aimed in the general vicinity of the body, said ultrasound transducer having affixed thereto a hood whose position is calibrated with respect to the ultrasound transducer, said hood having a plurality of reference points thereon which can be detected by said cameras for determining the position of the hood with respect to the reference coordinates, said reference points on said hood comprising a plurality of light sources.

12. A method as in claim 11 wherein said body is a human patient and said object is a correction such as a gallstone or kidney stone in the patient.

13. A system for localization of a stone in a human patient using ultrasound imaging of the stone for enabling the stone to be positioned with respect to a focal point of a shock wave system, and wherein the position of the focal point is calibrated with respect to reference coordinates, comprising first and second video cameras positioned with respect to a table of the system to provide separate images from the general vicinity of the focal point for providing images of an ultrasound transducer means which can be used to provide an ultrasound image of the stone, said cameras being calibrated with respect to the reference coordinates, ultrasound means including said ultrasound transducer means an circuit means for providing an ultrasound image of the stone and for enabling that image to be captured, system means connected to said video cameras for processing images of the ultrasound transducer means from said cameras and for calculating the location and orientation of the ultrasound transducer means with respect to the reference coordinates, and said ultrasound transducer means comprising an ultrasound transducer having a hood affixed thereto and wherein the position of the hood is calibrated with respect to the ultrasound transducer, said hood having a plurality of reference points thereon which can be detected and imaged by said cameras for enabling the position of the hood with respect to the reference coordinates to be determined by said system means.

14. A system as in claim 13 wherein said hood comprises an arcuate member spaced from the ultrasound transducer for enabling the ultrasound transducer to be grasped and operated by the operator while allowing a surface of the hood to be viewed by the cameras, said reference points comprising a plurality of sources on said surface which can be viewed and imaged by the cameras.

* * * * *